US00PP25184P3

(12) United States Plant Patent
Coiner

(10) Patent No.: US PP25,184 P3
(45) Date of Patent: Dec. 23, 2014

(54) FLORIBUNDA ROSE PLANT NAMED 'U.F.O.'

(50) Latin Name: *Rosa hybrida*
Varietal Denomination: U.F.O.

(76) Inventor: James W. Coiner, Covina, CA (US)

( * ) Notice: Subject to any disclaimer, the term of this patent is extended or adjusted under 35 U.S.C. 154(b) by 113 days.

(21) Appl. No.: 13/573,189

(22) Filed: Aug. 29, 2012

(65) Prior Publication Data

US 2014/0068825 P1 Mar. 6, 2014

(51) Int. Cl.
*A01H 5/00* (2006.01)

(52) U.S. Cl.
USPC ..... Plt./147; Plt./146

(58) Field of Classification Search
USPC ..... Plt./146, 147, 143, 141
See application file for complete search history.

*Primary Examiner* — Kent L Bell
(74) *Attorney, Agent, or Firm* — Christie, Parker & Hale, LLP

(57) ABSTRACT

A new variety of Floribunda rose suitable for garden decoration, having flowers of orange coloration.

1 Drawing Sheet

Classification: The present invention relates to a new *Rosa hybrida* plant.

Variety denomination: The new plant has the varietal denomination 'U.F.O.'.

BACKGROUND OF THE INVENTION

The present invention relates to a new and distinct Floribunda Rose variety which was originated by crossing as seed and pollen parents two unnamed, undistributed, unpatented seedlings. Among the novel characteristics possessed by the new variety which distinguish it from known other varieties is its initial attractive tight centered petals of coral coloration which transition into contrasting coral yellow or interior petals. The varietal denomination of the new rose is 'U.F.O.'.

SUMMARY OF THE INVENTION

Among the features which distinguish the new variety from other presently available and commercial rose cultivars known to the inventor is the following combination of characteristics: The plant is a bushy compact plant with upright spreading growth habit, suitable for outdoor garden decoration.

Asexual reproduction of the new variety by budding as performed in Kern County California, shows that the foregoing and other distinguishing characteristics come true to form and are established and transmitted through succeeding asexual propagations. 'U.F.O.' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Easy Living', by the following combination of characteristics: It has a unique bloom with flowers of high coloration, with robust vigorous growth habit and bright green foliage. The new variety may be distinguished from its parent plants primarily in flower color.

BRIEF DESCRIPTION OF ILLUSTRATION

The accompanying photograph, FIG. 1, illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of two year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers singly, sometimes in clusters of four to five or more per stem. Flowers are borne in regular rounded to pyramidal clusters on strong short to medium stems. Outdoors, the plant blooms abundantly and nearly continuously during the growing season. The flowers have a slight fruity fragrance.

BUD

The peduncle is about 3.1 cm to about 5.1 cm in length, of slender to average caliper. The peduncle has an observed diameter of 0.3 cm to 0.5 cm, with typical diameter of 0.4 cm. It is usually smooth, with some stipitate glands, and some hairs and prickles. Peduncle color is near between 144a and 148b. Before the calyx breaks, the bud is about 1.1 cm to about 2.1 cm in diameter at the widest point, about 1.3 cm to about 2.6 cm in length, and ovoid to globular in shape with a conspicuous neck. The surface of the bud bears some foliaceous appendages, stipitate glands and glandular bloom, usually with slender cut bristle-like foliaceous parts extending beyond the tip of the bud about ½ or more of its length. Bud color is near between 144a and 138a.

The sepals are about 2.7 cm to about 4.1 cm in length and about 1 cm to about 1.4 cm in width at the widest point. Sepal apex ends in elongated sharp point, about 0.1 cm wide and from 0.1 cm to 1 cm long. Observed and typical number of sepals are five. The outer surface color of the sepal is near between 144a and 138a. The inner surface color of the sepal is near between 137c and 138b. Sepal margins are lined with fine wooly tomentum, few stipitate glands and hairs.

The receptacle of the flower is of moderately short to medium length. Observed length ranges from 0.9 cm to 1.3 cm, with typical length of 1.1 cm. The observed diameter of the receptacles are 0.8 cm to 1.4 cm with typical diameter of 1.2 cm. The receptacle is globular in form. Its surface is somewhat smooth with moderately thin walls. The receptacle color is near between 144a and 138b.

As the petals open (after the calyx breaks), the bud is about 1.9 cm to about 2.7 cm in diameter at the widest point, about 3.2 cm to about 4.1 cm in length, and very moderately ovoid to globular in form. The color of the under surfaces of the newly opened petals is near between 32b 32c. The color of the upper surfaces of the newly opened petals is near between 23c-23d.

BLOOM

When fully open, the bloom ranges from about 7 cm to about 9 cm in diameter. Petalage is double with about 20 to 26 petals and about 1 to 4 petaloids irregularly arranged. When partially open, the bloom form is moderately cupped to globular, and the petals are somewhat tightly spiraled to cupped with petal edges somewhat rolled inward. When fully open, the bloom form is moderately cupped to full and globular, and the petals are somewhat tightly cupped to imbricated with petal edges moderately rolled outward.

PETALS

The substance of the petals is somewhat leathery crisp and of medium to thick thickness, with upper surfaces slightly satiny, and under surfaces slightly satiny to velvety. The petals are about 4.1 cm to about 6.2 cm in length and about 4.0 cm. to about 6.1 cm in width at the widest point. Petal margins are somewhat dentate.

The outer petals are very round in shape with apices rounded and usually slightly notched with one to two notches. At the base point where the petal attaches, there is a moderately small zone of approximately 0.5 cm of contrasting color change to near 23c-23d. The base attachment observed is from 0.2 cm to 0.4 cm wide, with typical width of 0.3 cm.

The inner petals are very broadly round in shape with apices rounded to flat and usually slightly notched with one to two notches. At the base point where the petal attaches, there is a zone of approximately 0.5 cm of slight color change of near 22c-22d. The base attachment observed is from 0.2 cm to 0.4 cm wide, with typical of 0.3 cm.

Petaloids are about 0.4 cm to about 1 cm in length and about 0.3 cm to about 0.8 cm in width at the widest point. Petaloids are shaped moderately round to cuneate with moderately rounded apices. Observed margins are smooth to slight ruffle, typically smooth; and tapering to a narrow base about 2 cm wide at the attachment. The observed texture of the petaloids surfaces are somewhat leathery crisp to very leathery crisp, typical texture being somewhat leathery crisp.

NEWLY OPENED FLOWER

The upper surface color of the outer petals is near between 23b and 23c. The under surface color of the outer petals is near between 32b and 32d. The upper surface color of the inner petals is near between 22b and 24b. The under surface color of the inner petals is near between 32b and 33b.

The upper surface color of the intermediate petals is near between 22b and 24b. The under surface color of the intermediate petals is near between 32b and 33b.

The under and upper surface color of the inner petals is near between 23c and 32d.

The under and upper surface color of the petaloids are similar in coloration to the upper and under surfaces of the intermediate and inner petals.

The general tonality of the newly opened flower is near between 32b and 32d.

THREE-DAY OLD FLOWER

The upper surface color of the outer petals is near between 23b and 23c. The under surface color of the outer petals is near between 32b and 32d. The under surface color of the inner petals is near between 22b and 24b. The under surface color of the inner petals is near between 32b and 33b.

The under and upper surface color of the petaloids are similar in coloration to the upper and under surfaces of the intermediate and inner petals.

The general tonality of the three-day-old flower is near between 32c and 32d.

On the spent bloom, the petals usually drop off cleanly except for some petaloids that persist.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 90) and are arranged regularly about the pistils; a few are mixed with petaloids or tucked in the calyx. The filaments are of very moderately medium to long length (about 0.5 cm to about 1.3 cm) most with anthers. Filaments are near between 13b and 12b in color. The anthers are somewhat medium for the class and all open approximately at the same time. Anther color is near between 29a and 30a when immature and near between 178c and 169a at maturity. Pollen is abundant and near between 17c and 15b in color.

FEMALE REPRODUCTIVE ORGANS

Pistils vary in number (average about 70). The styles are somewhat uneven, moderately average in length (about 0.4 to about 1.1 cm). Stigma color is near between 13c and 12b. Style color is near between 2c and 150d. Ovaries are usually enclosed in the calyx.

Hips have not been observed on this variety when grown in Wasco, Calif.

FOLIAGE

The compound leaves are usually comprised of three to five leaflets and are borne in normal quantities. The five-leaflet leaves are about 12.2 cm to about 15.6 cm in length and about 10.2 cm to about 12.6 cm in width at the widest point, very moderately crisp in texture and moderately semi-glossy to matte in finish. The terminal leaflets are about 5.4 cm to about 7.9 cm in length and about 3.1 cm to about 4.8 cm in width at the widest point, shaped somewhat obovate with very moderately obtuse to mucronate apices and very moderately obtuse bases. Their margins are somewhat serrate.

The upper surface color of the mature leaf is near between 137a and 137b. The under surface color of the mature leaf is near between 145a and 145b. The upper and under surface color of the young leaf is near between 138a and 138b, sometimes lightly suffused with near between 53a and 53b.

The rachis is somewhat slight to average in caliper. The observed rachis diameter is between 0.1 and 0.2 cm. Typical rachis diameter is 0.2 cm and somewhat rough. Observed length of rachis is between 4.8 cm and 7.3 cm, with typical length of 6.2 cm. The upper side is shallowly grooved with few hairs and stipitate glands on the edges of the grooves. The under side of the rachis is somewhat rough with few hairs and stipitate glands. The rachis color is near between 178b and 178c.

The observed stipules are about 0.8 cm to about 1.2 cm in length and somewhat medium width (about 0.5 cm to about 0.7 cm) with moderately short to medium straight points that usually turn out at an angle of less than 45 degrees away from the stem. Typical stipules are 1.1 in length and 0.05 cm in width. The stipules appear in pairs, with a thin leaf-like appendage that is attached to the base of each petiole. The stipules color is near between 141c and 141d.

The petiole is moderately slight to average in caliper and somewhat smooth. Observed diameter of petioles is between 0.1 cm to 0.3 cm, with typical diameter of 0.2 cm. Observed length of petiole is between 2.4 to 5.6 cm, with typical length of 3.1 cm. The upper side is moderately to shallowly grooved with few hairs and stipitate glands. The under side of the petiole is somewhat rough with some hairs and stipitate glands. The petiole color is near between 146a and 146c.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a compact upright medium height growth habit (about 110 cm to about 125 cm in height and about 55 cm to about 38 cm spread at the widest point), with moderate to full branching. It displays vigorous growth and the canes are of medium caliper for the class.

The color of the major stems is near between 141c and 141d. They bear several small prickles that are about 0.05 cm to about 1.0 cm in length. The prickles are almost straight and angled slightly upward with a very moderately short to medium length with rounded base; prickle color is near between 182b and 182d. The major stem bears many small prickles of similar shape and coloration. There are few fine hairs of similar shape and coloration.

The color of the branches is near between 141c and 141d. They bear some prickles which are of similar size and shape to the large prickles on the major stems; prickle color is near between 182b and 182d. There are few hairs of similar shape and coloration which are near between 182b and 182d.

The color of the new shoots is near between 186a and 186b sometimes heavily suffused with near between 190a and 190b. They bear several prickles which are of similar size and shape to the large prickles on the major stems; prickle color is near between 182d and 181d.

I claim:

1. A new and distinct Floribunda rose plant of the variety substantially as described and illustrated herein.

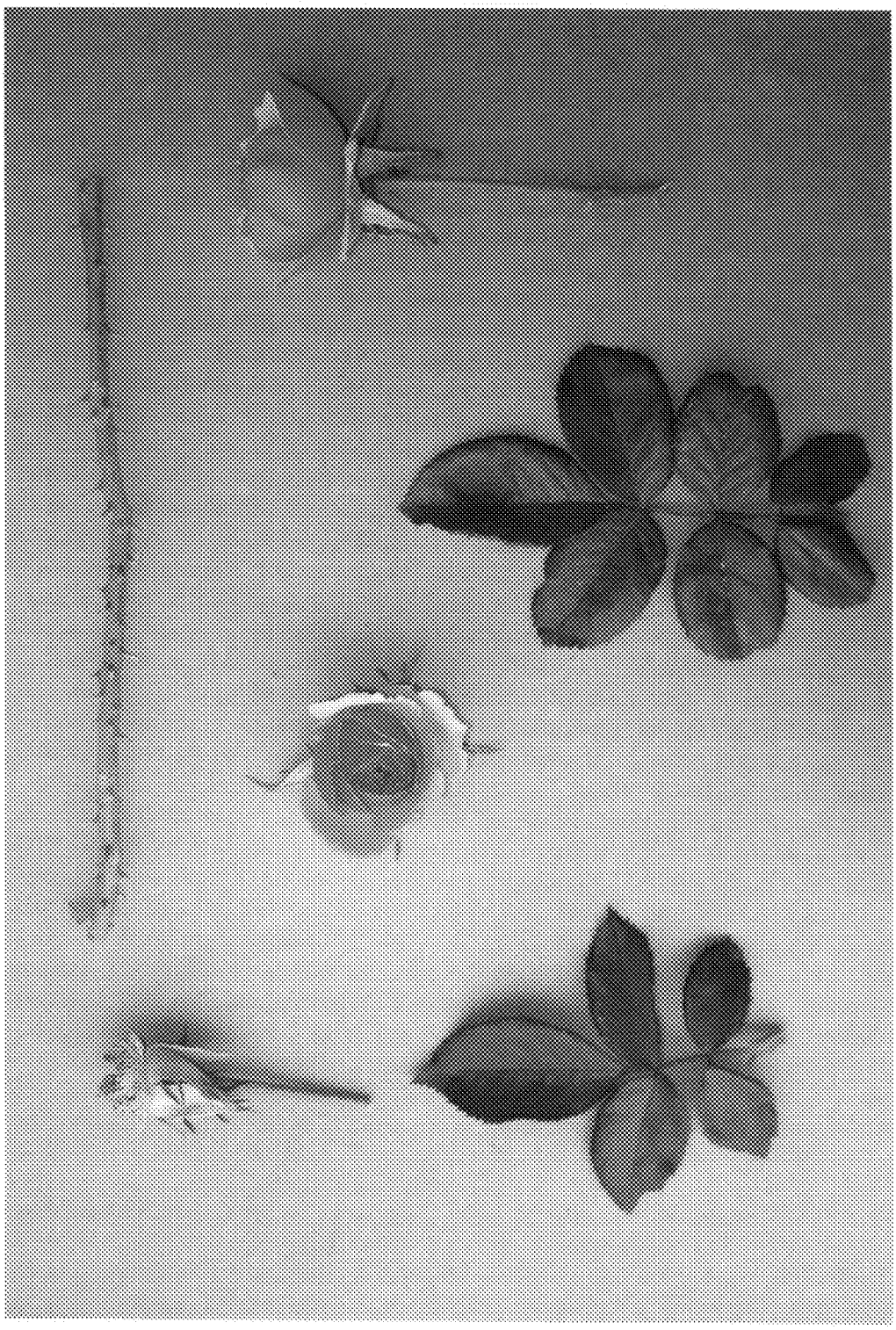

* * * * *